(12) United States Patent
Wang et al.

(10) Patent No.: US 10,943,342 B2
(45) Date of Patent: Mar. 9, 2021

(54) METHOD AND APPARATUS FOR IMAGE STITCHING OF IMAGES CAPTURED USING A CAPSULE CAMERA

(71) Applicant: CapsoVision, Inc., Saratoga, CA (US)

(72) Inventors: Kang-Huai Wang, Saratoga, CA (US); Yi Xu, Menlo Park, CA (US); Chenyu Wu, Sunnyvale, CA (US)

(73) Assignee: CapsoVision Inc., Saratoga, CA (US)

( * ) Notice: Subject to any disclaimer, the term of this patent is extended or adjusted under 35 U.S.C. 154(b) by 66 days.

(21) Appl. No.: 16/462,215

(22) PCT Filed: Nov. 30, 2016

(86) PCT No.: PCT/US2016/064245
§ 371 (c)(1),
(2) Date: May 17, 2019

(87) PCT Pub. No.: WO2018/101936
PCT Pub. Date: Jun. 7, 2018

(65) Prior Publication Data
US 2019/0287229 A1    Sep. 19, 2019

(51) Int. Cl.
*G06T 5/50* (2006.01)
*G06T 7/246* (2017.01)
(Continued)

(52) U.S. Cl.
CPC .......... *G06T 5/50* (2013.01); *A61B 1/00009* (2013.01); *A61B 1/041* (2013.01); *G06T 3/4038* (2013.01);
(Continued)

(58) Field of Classification Search
CPC ......... G06T 7/337; G06T 3/4038; G06T 5/50; G06T 7/0014; G06T 7/251; G06T 7/33;
(Continued)

(56) References Cited

U.S. PATENT DOCUMENTS

| 2014/0221742 A1 | 8/2014 | Bandy et al. |
| 2015/0221116 A1 | 8/2015 | Wu et al. |

(Continued)

OTHER PUBLICATIONS

T. Bergen and T. Wittenberg, "Stitching and Surface Reconstruction From Endoscopic Image Sequences: A Review of Applications and Methods", Jan. 2016, IEEE Journal of Biomedical and Health Informatics, vol. 20, No. 1, pp. 304-321. (Year: 2016).*

*Primary Examiner* — Brenda C Bernardi
(74) *Attorney, Agent, or Firm* — Blairtech Solution LLC (57) ABSTRACT

A method and apparatus of processing images captured from human gastrointestinal (GI) tract by a capsule camera are disclosed. High frame-rate images captured from human gastrointestinal (GI) tract by a capsule camera are received for processing. The high frame-rate images comprise first images at a first spatial resolution corresponding to a regular frame rate and second images at a second spatial resolution, the first images and the second images are interleaved, and the second spatial resolution is lower than the first spatial resolution. Motion models among the high frame-rate images are derived by applying image registration to the high frame-rate images. The high frame-rate images are stitched according to the motion models to generate stitching outputs comprising stitched images and non-stitched images. The stitching outputs are provided.

22 Claims, 4 Drawing Sheets

(51) Int. Cl.
    *G06T 7/33*         (2017.01)
    *A61B 1/00*       (2006.01)
    *A61B 1/04*       (2006.01)
    *G06T 3/40*       (2006.01)
    *G06T 7/00*       (2017.01)

(52) U.S. Cl.
    CPC ............ *G06T 7/0014* (2013.01); *G06T 7/246* (2017.01); *G06T 7/251* (2017.01); *G06T 7/33* (2017.01); *G06T 7/337* (2017.01); *G06T 2207/10016* (2013.01); *G06T 2207/10068* (2013.01); *G06T 2207/20221* (2013.01); *G06T 2207/30092* (2013.01)

(58) Field of Classification Search
    CPC ........... G06T 7/246; G06T 2207/30092; G06T 2207/20221; G06T 2207/10016; G06T 2207/10068; A61B 1/041; A61B 1/00009
    See application file for complete search history.

(56) References Cited

U.S. PATENT DOCUMENTS

| | | | |
|---|---|---|---|
| 2015/0334276 A1 | 11/2015 | Ecker et al. | |
| 2016/0295126 A1* | 10/2016 | Wang | H04N 5/23238 |
| 2017/0055814 A1* | 3/2017 | Wang | G06K 9/52 |
| 2018/0174318 A1* | 6/2018 | Wang | G06T 7/62 |

\* cited by examiner

METHOD AND APPARATUS FOR IMAGE STITCHING OF IMAGES CAPTURED USING A CAPSULE CAMERA

CROSS REFERENCE TO RELATED APPLICATIONS

The present invention is related to PCT Patent Application, Ser. No. PCT/US14/38533, filed on May 19, 2014, which claims priority to U.S. Provisional Patent Application, Ser. No. 61/828,653, filed on May 29, 2013. The present invention is also related to U.S. Non-provisional patent application Ser. No. 14/675,744, filed on Apr. 1, 2015. The PCT Patent Application, U.S. Provisional Patent Application and U.S. Non-provisional Patent Application are hereby incorporated by reference in their entireties.

FIELD OF THE INVENTION

The present invention relates to image stitching for images captured by a capsule camera while the capsule camera travels through the human gastrointestinal (GI) tract. In particular, the present invention is related to techniques to improve the stitching efficiency so as to reduce the number of images at the stitching output.

BACKGROUND AND RELATED ART

Capsule endoscope is an in vivo imaging device which addresses many of problems of traditional endoscopes. A camera is housed in a swallowable capsule along with a radio transmitter for transmitting data to a base-station receiver or transceiver. A data recorder outside the body may also be used to receive and record the transmitted data. The data primarily comprises images recorded by the digital camera. The capsule may also include a radio receiver for receiving instructions or other data from a base-station transmitter. Instead of using radio-frequency transmission, lower-frequency electromagnetic signals may be used. Power may be supplied inductively from an external inductor to an internal inductor within the capsule or from a battery within the capsule. In another type of capsule camera with on-board storage, the captured images are stored on-board instead of transmitted to an external device. The capsule with on-board storage is retrieved after the excretion of the capsule. The capsule with on-board storage provides the patient the comfort and freedom without wearing the data recorder or being restricted to proximity of a wireless data receiver.

The images and data after being acquired and processed are usually displayed on a display device for a diagnostician or medical professional to examine. However, each image only provides a limited view of a small section of the GI tract. It is desirable to form (stitch) a single composite picture with a larger field of view from multiple capsule images. A large picture can take advantage of the high-resolution large-screen display device to allow a user to visualize more information at the same time. An image stitching process may involve removing redundant overlapped areas between images so that a larger area of the inner GI tract surface can be viewed at the same time in a single composite picture. In addition, a large picture can provide a complete view or a significant portion of the inner GI tract surface. It should be easier and faster for a diagnostician or a medical professional to quickly spot an area of interest, such as a polyp. Moreover, captured images may have, for example, 30,000 frames. It will take users more than one hour for review. An image stitching process can thus reduce frame numbers and accelerate the review procedure.

However tissues in the GI tract often deform. Also the capsule movement inside the GI track is not steady. The camera may rotate and hesitate inside the human GI tract. In addition, while the GI tract is supposedly cleaned well before administering the capsule, various objects such as food residues and bubbles may still appear in the images. Therefore, the images captured by the capsule camera are non-ideal from the image models used in various image composition or image stitching processing. It is desirable to develop methods that take into consideration of the fact that the captured images are non-ideal and improve the processing or algorithm convergence speed.

SUMMARY OF INVENTION

A method and apparatus of processing images captured from the human gastrointestinal (GI) tract by a capsule camera are disclosed. High frame-rate images captured from the human gastrointestinal (GI) tract by a capsule camera are received for processing. The high frame-rate images comprise first images at a first spatial resolution and second images at a second spatial resolution, the first images and the second images are interleaved, and the second spatial resolution is lower than the first spatial resolution. Motion models among the high frame-rate images are derived by applying image registration to the high frame-rate images. The high frame-rate images are stitched according to the motion models to generate stitching outputs comprising stitched images and non-stitched images. The stitching outputs are provided.

Image registration applied to the high frame-rate images may comprise deformable registration and motion estimation. The deformable registration can be applied prior to or after the motion estimation. The deformable registration and the motion estimation can be applied to the high frame-rate images iteratively until a stop criterion is met. The motion estimation may correspond to global translational motion estimation. The motion estimation may also correspond to affine transformation.

In one embodiment, the stitching is only applied to the first images. When image registration is applied to the high frame-rate images, the image registration is performed at both the first spatial resolution and the second spatial resolution. However, stitching is always performed at the first spatial resolution. The information for identifying at least partial membership belonging to each stitched image can be provided along with the stitching outputs. If any non-stitched image in the stitching outputs belongs to the second images, the non-stitched image is removed from the stitching outputs. The second spatial resolution can be equal to one half or one quarter of the first spatial resolution horizontally and vertically. Furthermore, the second images are captured with lower bit-depth compared to the first images.

According to another method, similar steps as the first method are performed. However, the second spatial resolution can be lower than or equal to the first spatial resolution. Furthermore, if any non-stitched image in the stitching outputs belongs to the second images, the non-stitched image is removed from the stitching outputs.

According to yet another method, the method comprises image capturing and image processing. High frame-rate images are captured using a capsule camera while the capsule camera is travelling through the human gastrointestinal (GI) tract after swallowed by a human subject. High frame-rate images comprise first images at a first spatial resolution and bridging images at a second spatial resolution. The first images and the bridging images are interleaved, and the second spatial resolution is lower than the first spatial resolution. The registration process and stitching process can be the same as before. In one embodiment, the bridging images are captured by reducing light source energy illuminating a scene in a field of view (FOV) of the capsule camera comparing to the first images. For example, the light source energy can be reduced by at least half for the bridging images. Pixel values of the first images or the bridging images are adjusted to take into consideration of different light source energies. If the high frame-rate images captured are compressed, the bridging images can be compressed using a higher compression ratio compared to the first images. According to another embodiment, the bridging images can be captured with lower bit-depth compared to the first images. Pixel values of the first images or the bridging images are adjusted to take into consideration of different bit-depths.

DETAILED DESCRIPTION OF THE INVENTION

In the following description, various aspects of the present invention will be described. For purposes of explanation, specific configurations and details are set forth in order to provide a thorough understanding of the present invention. Well known features may be omitted or simplified in order not to obscure the present invention.

A review of general technical approaches to image registration and stitching can be found in "Image Alignment and Stitching: A Tutorial", by Szeliski, Microsoft Research Technical Report MSR-TR-2004-92, Dec. 10, 2006.

Sequential image stitching is the process often used for image stitching. It takes a few sequential images captured by camera as input and composes them seamlessly onto a big canvas. This process reduces the number of image frames by mosaicking similar consecutive images together into a "big picture". Thus, it reduces the time for a doctor or a medical professional to examine the stitched images. The input images may correspond to panoramic images captured using multiple cameras (e.g. four cameras with FOV separated by 90° to cover a 360° panoramic view). Furthermore, it is assumed that each set of perspective images captured concurrently by the multiple cameras has been properly stitched into a panoramic image. The panoramic images are to be sequentially stitched in this case.

Before image mosaicking can be applied to images, the correspondences between the images have to be identified. The process to identify the correspondence is called image registration. In image registration, corresponding features, objects or areas from two images are detected and identified first. The two images can then be aligned by warping one image to another according to some mathematical models. Model parameters have to be calculated from the captured images. Because the gastrointestinal tract is constantly undergoing deforming motion, deformable registration that accounts for non-linear spatial transformation is needed to align two consecutive images. Accordingly, an intensity-based deformable registration framework is preferred to a feature-based one since good features are not always present in gastrointestinal images. The transformation model preferred is free-form deformation cubic B-splines. A gradient-based implicit Euler method can be used for optimization. The energy model uses correlation coefficient as the difference measurement and penalizes Laplacian of the displacements for regularization. For convenience, a first frame is referred as reference R, and the second frame is referred as float image F. The deformable registration deforms the float image F until it matches reference R, and leave reference R unchanged.

The images captured by capsule camera not only contain deformation, but also have global rigid transformation, which is caused by camera motion inside the gastrointestinal tract. In order to achieve good image registration results, a step that estimates the global transformation, more specifically, translation between two consecutive image frames is introduced. Methods that estimate rigid transformation by minimizing certain similarity measure (e.g., cross correlation, mutual information, etc.) often fail to yield reasonable results because deformation is generally greater than global transformation. In order to overcome this issue, a simple method based on deformable registration is used. For each pair of input images, we assume they completely overlap and run the deformable registration at a lower resolution (e.g., 1/16 of the original resolution). A displacement vector is calculated based on the optimized deformation for each pixel. The average displacement is then derived and is used as the global translation between two images.

The recovered translation is then applied to the input image and the deformable registration is re-computed at the overlapped region. In our experiments, this method is found to be effective when the global translation is small. However, when the translation is large, it cannot obtain accurate translation. Nevertheless, the recovered translation is usually in the same direction as the true one. Therefore, registration is still improved by translating the float image F closer to its true position. The deformable registration can be applied at a selected set of global offset locations and a best location that achieves a best match is selected to determine both the deformable registration and motion estimation. For example, the deformable registration can be applied at a few global offsets (e.g. [0,−10], [0 0], [0 10]) and use the best match as the global motion. Its associated deformable registration is used as the best registration as well.

During the registration process, the current image frame is designated as reference R and the next frame is designated as float image F. The aforementioned deformable registration is applied between R and F. If the registration is good enough, frames R and F are stitched together to form a new reference R. The next image frame becomes float image F. If the registration is not good enough, the current reference R is written to output and frame F becomes the new reference frame R. In this way, consecutive input frames are stitched onto a bigger canvas in a greedy fashion. The current reference R written to the output becomes a stitching output image. This stitching output image may correspond to a stitched image if two or more images have been stitched to form this stitching output image. This stitching output image may correspond to a non-stitched image if the corresponding reference R is never stitched with any image.

To determine whether the registration is good, several criteria may be used. For example, the overlap between two images after registration can be computed. If the overlap percentage is below a certain threshold (e.g. 75% of the reference image), the registration is rejected. The maximum displacement of the deformation may also be calculated. If large deformation (e.g. 40 pixels) is found, the registration is rejected. In yet another example, a quality measure of the registration can be calculated. The quality measure may be related to information preserved for clinical purpose. For example, a measure that is capable of detecting a small amount of changes between two frames. This measure can be computed for three channels (e.g. RGB) of the difference image between R and warped F. An average filter of 30×30 pixels can be applied to the difference image and the maximum difference value is used as the score. The registration can be rejected if the score exceeds a threshold (e.g. 0.18).

Once the images are aligned by deformable registration, the images can be mosaicked, i.e., stitched. There are two widely used image mosaicking techniques. The first method is blending, which aims at minimizing artifacts by smoothing the transitions between images (e.g., feathering or alpha blending). The second approach is optimal seam, which searches for an optimal seam in the overlap region on which the two images match the best.

Feathering or alpha blending computes a per-pixel alpha value that serves as the weight of blending between reference frame R and warped float image F, which is referred to as an alpha map A in this disclosure. The blended result I can be written as $$I = F \times (1-A) + R \times A \quad (1)$$

where x denotes element-wise multiplication. To compute A, the contours of the R and F on a big blank canvas are first computed. The distance transforms on both contours, DR and DF are then computed. Finally, A is computed based on the distance to each contour:

$$A = \frac{D_R}{D_R + D_F}. \quad (2)$$

One problem with alpha blending is that high frequency details are potentially smeared because of the blending. Also, even minor misalignment will lead to a blurred image. This will become worse when blending is applied to a relatively large number of images.

The optimal seam technique is based on the minimum error boundary cut method disclosed by Efros and Freeman ("Image Quilting for Texture Synthesis and Transfer", Alexei A. Efros and William T. Freeman, *Proceedings of the 28th Annual Conference on Computer Graphics and Interactive Techniques* (SIGGRAPH), Pages 341-346, 2001). The key idea is to find a cut on the pixels, where the two images best match. The output image can be composed by placing only one image at each side of the cut without any blending or by applying blending on a narrow band around the seam. At each pixel location within the overlap region, error is defined as the sum of squared differences of the RGB channels between the two pixels.

To stitch the deformed F with R, the parts of F that need to be attached to the reference R are first identified. Because the deformation can have arbitrary shape, there might be more than one such attachment. A connected component analysis on the attachment can be performed and each component is treated as one object.

For each object, the starting and ending points, where the attachment object's contour enters and leaves reference image R, can be found. These points can be either a single pixel (most cases) or a set of connected pixels when the part of the contour of the float F aligns with that of R. One of them can be set as the source and the other is set as the sink. The minimum cut algorithm is run on the overlapped region to find a path that goes from any pixel of the source to any pixel of the sink. After the optimal path is computed, the pixels enclosed by the path and the attachment object are replaced with pixels from the float image F. To remove any remaining visual seams, feathering on a narrow band of pixels (e.g. 10 pixels) along the path can be applied. To avoid multiple paths intersect with each other, all the computed path locations are recorded and set to have infinite error the during minimum error boundary cut process. In this way, any new path will not intersect with existing ones.

The above-mentioned image stitching technique has been applied to sets of image sequences captured in vivo using a capsule camera. The image sequences are captured at a frame rate of two frames per second to generate a total number of images in the order about 30,000 images. Based on the test, roughly 20% redundancy can be removed, i.e., the total number of stitching output images being about 20% less.

For capsule camera application, the small device has to travel through the human gastrointestinal (GI) tract in long hours (e.g. 10 hours or more) and takes a large number of images (e.g. 30,000 or more). All the operations are supported by small button battery or batteries inside the capsule housing. Furthermore, all the images have to be taken using light source(s) within the capsule camera. Therefore, the power source becomes a very precious resource for the system. In practice, a capsule system can only afford to capture images at a very low frame rate (e.g. 2 frames per second). Though the capsule camera travels very slowly in the GI track, registration between consecutive images is still very difficult to perform well due to various reasons, such as the low frame rate causing large relative differences between images.

One technique to improve the stitching efficiency is to increase the frame rate so that it may result in better registration and improved stitching efficiency. However, increasing the frame rate will also result in more images captured, which appears to conflict with the goal of a smaller number of stitching output images. Nevertheless, if the additional redundancy removal outweighs the increased number of captured images, net gain in redundancy removal can be achieved. For example, if the frame rate is increased to 6 frames/sec (i.e., three times of 2 frames/sec), the total number of frames captured during the same period of time will be increased to three times. At 2 frames/sec, it is found that about 20% of the images can be stitched. If the total number of captured images is 30,000, the number of stitching output images will be 24,000. With the increased frame rate, it is anticipated to result in better registration due to smaller changes between two neighboring images at a shorter frame period. In order to achieve the goal of smaller number of stitching output images, the percentage of stitched images has to be increased substantially. In the above example, the percentage of stitched images has to be greater than 73.33%. If the images that can be stitched are hypothetically at 60%, the stitching output images for this case become 36,000 (i.e., 90,000×(1-60%)), which is substantially higher than the conventional approach. Therefore, it is desirable to develop a system that can practically achieve net gain in redundancy removal using high frame rate capturing.

As mentioned previously, the capsule camera has very limited resources in terms of power and storage. The capsule camera is powered by one or more button batteries that are expected to last more than 10 hours during the course of imaging the human GI tract. The batteries will be used by light sources (e.g. LED) to illuminate the scenes being imaged. The batteries are also used by the image sensor and processor for capturing and processing images. It is very difficult for the capsule camera to be able to double or even to triple the frame rate.

The idea of high frame-rate capture is mainly intended to increase registration quality between neighboring images by reducing the frame period between the two images so that more images can be stitched. Accordingly, the present invention discloses a technique to improve the efficiency of stitching without causing too much burden on additional image data and/or processing resources. Based on the present invention, additional "bridging images" are captured to assist image registration and derivation of motion models. The bridging images do not have to be captured in full resolution. In order to conserve the precious system resources such as storage and battery power, the bridging images are captured at reduced spatial resolution according to preferred embodiments. Nevertheless, technology will gradually evolve and the system may be able to afford capturing bridging images at full resolution in the future.

Figure 1A:
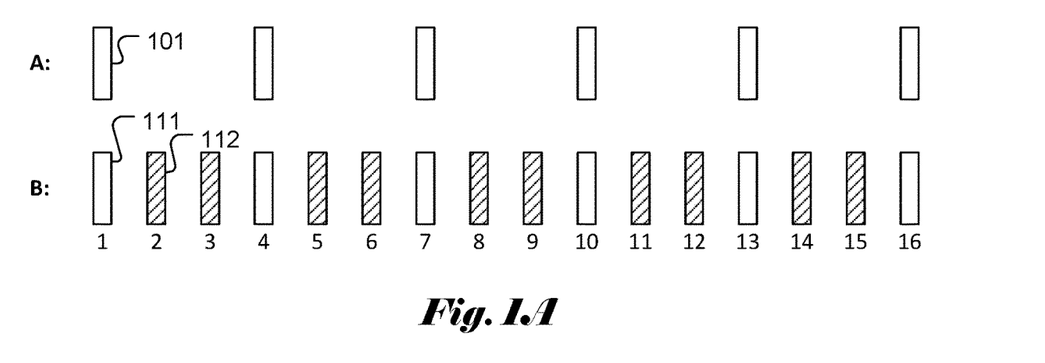
FIG. 1A illustrates an example of a regular image sequence and a high frame-rate image sequence, where the high frame-rate image sequence comprises regular images and bridging images.
Figure 1B:
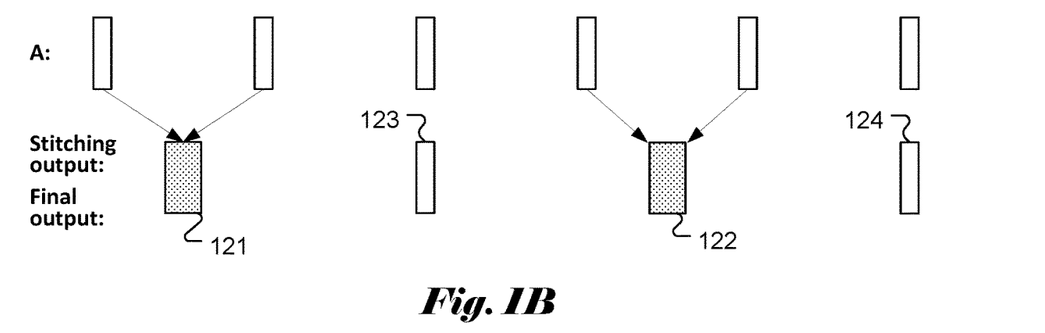
FIG. 1B illustrates exemplary image stitching for the regular image sequence.

FIG. 1A illustrates an example of capturing regular images in a conventional system and capturing regular images and bridging images in an interleaved fashion according to an embodiment of the present invention. In FIG. 1A, image sequence A corresponds to a regular sequence, where each image 101 represents a regular image at full resolution. Image sequence B corresponds to a high frame-rate image sequence, which comprises interleaved regular images (111) and bridging image (112). In this example, the high frame rate is three times of the regular frame rate. FIG. 1B illustrates an example of image stitching for the regular frame-rate images corresponding to a conventional approach. The first two images are stitched into stitched image 121; the next image is non-stitched (123); the following two images are stitched into stitched image 122; and the last image is non-stitched (124). In this example, the stitching output images consist of two stitched images (121 and 122) and two non-stitched images (123 and 124). All stitched images and non-stitched images are at the high resolution. Since the regular frame-rate images are captured at a relatively low frame rate, each image may contain pathological importance. Therefore, all stitching output images, regardless of stitched or non-stitched images, will be retained as final output images. In other words, there will be four final output images based on the conventional approach. In FIG. 1B, the stitched images are shown with a wider block size to indicate that the stitched images are larger. Nevertheless, the block size of the stitched images as shown in FIG. 1B is not intended to show in proportion to the actual stitched image size.

Figure 1C:
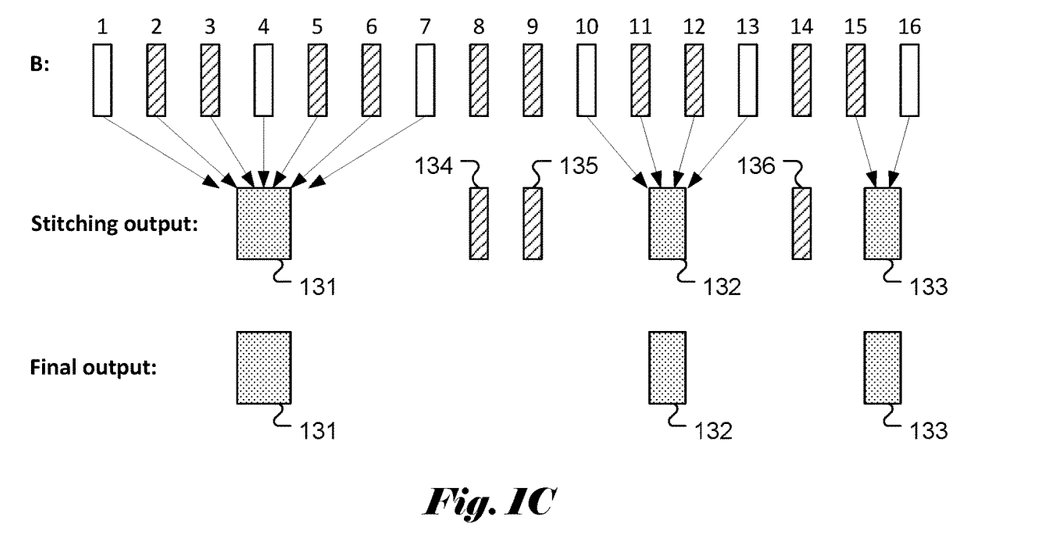
FIG. 1C illustrates exemplary image stitching for the high frame-rate image sequence, where the bridging images provide additional information for estimating motion models between two regular images.

FIG. 1C illustrates an example of image stitching for the high frame-rate images. The first seven images are stitched into stitched image 131; the next two bridging images are non-stitched (134 and 135); the following four images are stitched into stitched image 132; the following bridging image is non-stitched (136); and the last two images are stitched into stitched image 133. When image registration is applied to the high frame-rate images, the registration between regular images is assisted by the intervening bridging images. For example, registration can be applied between regular image 1 and bridging image 2, between bridging images 2 and 3, and between bridging image 3 and regular image 4. With the intervening bridging images 2 and 3, it is expected to improve the registration between regular images 1 and 4. The stitching can be applied to the high frame-rate images, i.e., both regular images and bridging images. However, in one preferred embodiment, the stitching is only applied to the regular images. After two images are stitched, image stitching can be further performed based on an already stitched image and a new image (either a regular image or a bridging image). In the example shown in FIG. 1C, the stitching output images consist of stitched images 131-133 and non-stitched images 134-136. Since the bridging images are captured at reduced resolution, the images can be dropped from the final output if the non-stitched image is a bridging image. Accordingly, there are three stitched images 131-133 at the final output. Compared to the conventional approach, an embodiment according to the present invention as shown in FIG. 1C stitches one less image.

In order to reduce storage as well as required processing power, the bridging images are captured at 2:1 or 4:1 reduced resolution horizontally and vertically. In the case of 4:1 reduced resolution horizontally and vertically, each bridging image corresponds to 1/16 of the regular-size image. Therefore, while the frame rate is increased to three times of the original frame rate, the total image data are only increased by 12.5%. For a capsule camera with an on-board storage, the captured images will be stored in the on-board memory. After the capsule camera is excreted from the human body and retrieved, the images stored on-board will be retrieved for processing and/or viewing. In order to conserve storage space, the images may be stored in a compressed format. For the capsule camera with a wireless transmitter, the images captured will be transmitted to a wireless receiver outside the human body. For example, the patient may wear a wireless body pack to receive the images transmitted from the capsule camera while the capsule camera travels inside the human body. The images are then retrieved from the wireless pack to a base station for processing and/or display.

Besides capturing the bridging images at reduced resolution, the system can further conserve the power by capturing the bridging images with reduced light source energy that illuminates a scene in the field of view (FOV) of the capsule camera. For example, the light source energy can be reduced to cause the expected photon-generated charges in the pixels to become about half compared to the original light source energy. Therefore, the intensities of the bridging images can be up-scaled by 2 to match the intensities of the regular images, for example by multiplying by 2 of the pixel value output from the sensor or by increasing the sensor readout gain by 2. It is also possible to scale down the intensities of the regular images by 2 to match that of the bridging images during image registration.

According to yet another embodiment, the system may reduce energy by capturing the bridging images with less bit-depth. For example, the regular images may be captured at 10 bits per pixel while the bridging image may be captured at 9 bits per pixel. When the image is captured with 9 bits, the whole gamut is divided into 512 levels. When the image is captured with 10 bits, the whole gamut is divided into 1024 levels. During processing, the data associated with the bridging images may be left-shifted by 1 bit, or by rounding off, during registration to match with the data associated with the regular images. In this case, a "0" can be stuffed to as the LSB to the 9-bit output to convert it to 10 bits. Alternatively, the data corresponding to the regular images may be shifted down by 1 bit during registration to match with the data corresponding to the bridging images. In this case, the LSB of the 10-bit output can be dropped or rounded off to convert it into 9 bits.

According to yet another embodiment, when image compression is applied to captured images, the bridging images may use higher compression ratio compared to the regular images. Since the bridging images are mainly used for registration, the image quality may not be so critical. Accordingly, the bridging images can afford larger distortion caused by image compression.

While the registration for the high frame-rate images may take advantage of the additional bridging images to provide intermediate motion models between two regular images, the possibility to stitch two regular images has been improved. Nevertheless, it is not guaranteed that bridging images always help to improve stitching. Accordingly, in one embodiment, registration directly between two regular images is checked if the two regular images with the intervening bridging images cannot be stitched. In other words the system using bridging images to assist image stitching will never be worse than the conventional approach in any case according to this embodiment.

For the stitching output images, if there is any non-stitched bridging image, the non-stitched bridging image will be dropped from the final output. If there is any non-stitched regular image, the non-stitched regular image will be kept in the final output. The output order of the final images can be in the processing order. In other words, when a stitched image is generated and no more new image can be stitched to this stitched image, the stitched image can be outputted. If a regular image is found to be non-stitched, the non-stitched regular image is outputted. Therefore, the final output images consist of interleaved stitched images and non-stitched images.

After images are stitching into a stitched image, the correspondence between the stitched image and its membership images (i.e., images being stitched into the stitched image) may not be known after stitching is done. However, a doctor or a medical professional may be interested in pathological information in the original membership images associated with the stitched image. Therefore, according to an embodiment of the present invention, the membership or at least partial membership belonging to each stitched image is provided along with the stitching output. The original images are often stored even for the images that are stitched into stitched images. In one embodiment, the membership information associated with each stitched image is stored along with the data of the stitched image or stored separately so that the membership information can be used to retrieve the individual original images. Similarly, information regarding to the regular images that are not stitched can be stored. This information may be useful to avoid the need for storing non-stitched regular images and the corresponding original regular images.

For image stitching, the process mainly comprises two tasks: registration and stitching (i.e., mosaicking). The registration usually involves intensive computations regardless of whether it is intensity-based or feature-based. Images of the GI walls captured using a capsule camera typically contain very few features. Due to peristalsis, the images of the intestine walls are often deformed from frame to frame. Accordingly, deformable registration is required for images of the GI tract, which further increases the complexity of image registration. On the other hand, after registration, the motion models are known, the stitching process (i.e., mosaicking) is relatively easy. The stitching process can be potentially performed locally at a display terminal (e.g. a laptop computer) for a doctor or medical professional to view. Accordingly, in one embodiment, the two main tasks, i.e., registration and mosaicking are performed separately. In particular, the registration is performed by a more powerful processing station such as a server, a high-end computer or multiple computers arranged to work jointly or collaboratively. The registration results can be stored or transmitted so that the image mosaicking can be performed using the registration results. In this case, the original regular images are assumed to be locally available so that the mosaicking process can be applied. The processing can be done in a cloud environment, where a user may upload the high frame-rate images to a cloud server and receive back the derived registration results. The mosaicking is then done in real-time locally.

As mention previously, the images captured by capsule camera not only contain deformation, but also have global rigid transformation. Accordingly, the global transformation is introduced to work with deformation. In one embodiment, global transformation and deformable registration are applied iteratively. The global transformation can be applied first and followed by the deformable registration. Alternatively, the deformable registration can be applied first and followed by the global transformation. The iterative process can be terminated when a pre-defined criterion is met. Global translation motion has been disclosed as a form of global translation. In another embodiment, the affine transformation may also be used for the motion estimation. In yet another embodiment, a pre-defined set of global transformations can be used and the deformable registration is performed at each transformation. The global transformation that achieves the best match is used as the selected global transform. Its associated deformable registration is used as the selected deformable registration.

Figure 2:
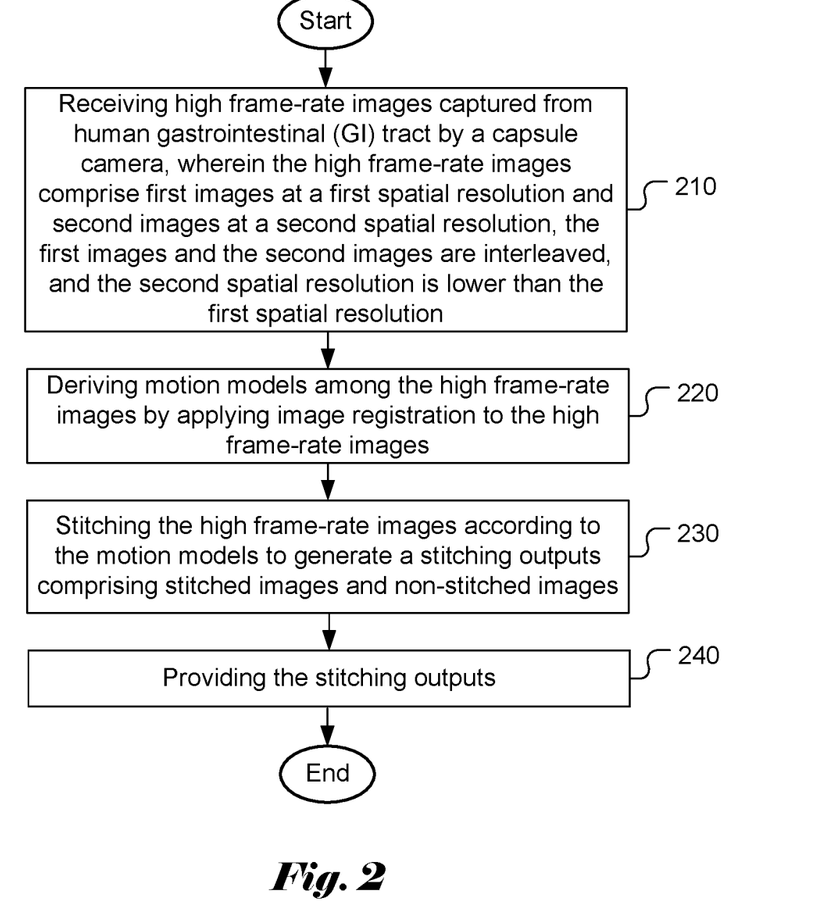
FIG. 2 illustrates an exemplary flowchart for an image sequence stitching system according to an embodiment of the present invention, where the bridging images have lower spatial resolution.

FIG. 2 illustrates an exemplary flowchart for an image sequence stitching system according to an embodiment of the present invention, where the bridging images have lower spatial resolution. The system receives high frame-rate images captured from human gastrointestinal (GI) tract by a capsule camera in step 210. The high frame-rate images comprise first images at a first spatial resolution and second images at a second spatial resolution, the first images and the second images are interleaved, and the second spatial resolution is lower than the first spatial resolution. Motion models among the high frame-rate images are derived by applying image registration to the high frame-rate images in step 220. The high frame-rate images are stitched according to the motion models to generate stitching outputs comprising stitched images and non-stitched images in step 230. The stitching outputs are provided in step 240. The stitching outputs can be displayed for a doctor or a medical professional to view.

Figure 3:
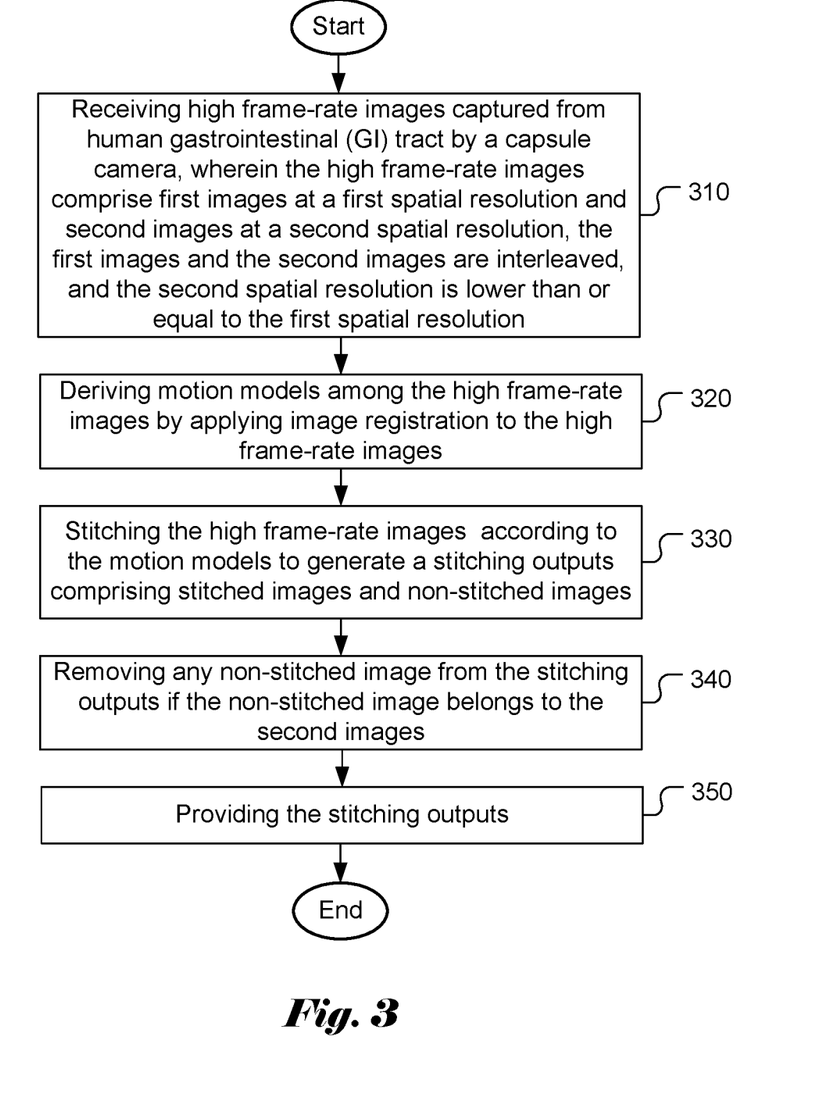
FIG. 3 illustrates an exemplary flowchart for another image sequence stitching system according to an embodiment of the present invention, where a non-stitched image is removed from the stitching output if the non-stitched image is a bridging image.

FIG. 3 illustrates an exemplary flowchart for an image sequence stitching system according to another embodiment of the present invention, where a non-stitched image is removed from the stitching output if the non-stitched image is a bridging image. This system is similar to that in FIG. 2. However, the bridging images may have the same spatial resolution as the first images. This system also includes a step to remove non-stitch image from the stitching outputs if the non-stitched image is a bridging image. The system receives high frame-rate images captured from human gastrointestinal (GI) tract by a capsule camera in step 310. The high frame-rate images comprise first images at a first spatial resolution corresponding to a regular frame rate and second images at a second spatial resolution, the first images and the second images are interleaved, and the second spatial resolution is lower than or equal to the first spatial resolution. Motion models among the high frame-rate images are derived by applying image registration to the high frame-rate images in step 320. The high frame-rate images are stitched according to the motion models to generate stitching outputs comprising stitched images and non-stitched images in step 330. Any non-stitched image is removed from the stitching outputs if the non-stitched image belongs to the second images in step 340. The stitching outputs are provided in step 350.

Figure 4:
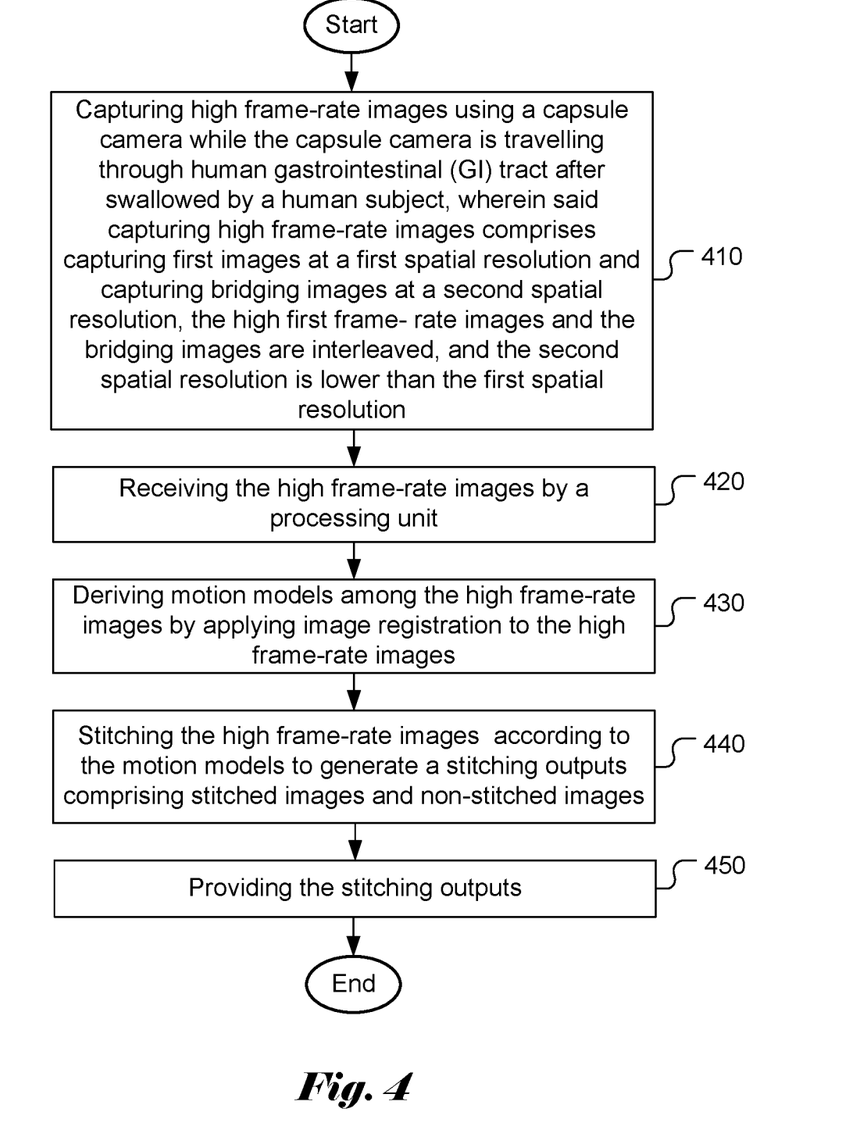
FIG. 4 illustrates an exemplary flowchart for another image sequence stitching system according to an embodiment of the present invention, where the system comprises image capturing and image processing.

FIG. 4 illustrates an exemplary flowchart for another image sequence stitching system according to an embodiment of the present invention, where the system comprises image capturing and image processing. The system captures high frame-rate images using a capsule camera while the capsule camera is travelling through human gastrointestinal (GI) tract after swallowed by a human subject in step 410. Capturing high frame-rate images comprises capturing first images at a first spatial resolution and capturing bridging images at a second spatial resolution, the first images and the bridging images are interleaved, and the second spatial resolution is lower than the first spatial resolution. The high frame-rate images are received by a processing unit in step 420. Motion models among the high frame-rate images are derived by applying image registration to the high frame-rate images by the processing unit in step 430. The high frame-rate images are stitched according to the motion models to generate stitching outputs comprising stitched images and non-stitched images in step 440. The stitching outputs are provided in step 450.

The above method can be implemented as computer programs on a machine-readable medium to be executed on a computer. The term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that causes the machine to perform any one or more of the methodologies of the present invention. The machine-readable medium includes any mechanism that provides (i.e., stores and/or transmits) information in a form readable by a machine (e.g., a computer, tablet, smartphone, etc.). For example, a machine-readable medium includes memory (such as described above), optical storage media or flash memory devices can be used as the machine-readable medium.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art. Accordingly, the specification and drawings are to be regarded in an illustrative rather than a restrictive sense.

The invention may be embodied in other specific forms without departing from its spirit or essential characteristics. The described examples are to be considered in all respects only as illustrative and not restrictive. Therefore, the scope of the invention is indicated by the appended claims rather than by the foregoing description. All changes which come within the meaning and range of equivalency of the claims are to be embraced within their scope.

The invention claimed is:

1. A method of processing images captured from human gastrointestinal (GI) tract by a capsule camera, the method comprising:
   receiving high frame-rate images captured from human gastrointestinal (GI) tract by a capsule camera, wherein the high frame-rate images comprise regular images and bridging images, wherein the regular images and the bridging images are interleaved, and wherein the bridging images are captured with a lower spatial resolution than the regular images;
   deriving motion models among the high frame-rate images based on image registration, wherein the image registration comprises target image registration between bridging images or between regular images and bridging images;
   stitching the high frame-rate images according to the motion models to generate stitching outputs comprising stitched images and non-stitched images; and
   providing the stitching outputs.

2. The method of claim 1, wherein the image registration applied to the high frame-rate images comprises deformable registration and motion estimation.

3. The method of claim 2, wherein the deformable registration is applied prior to the motion estimation.

4. The method of claim 2, wherein the deformable registration is applied at a selected set of global transformations and a best global transformation that achieves a best match is selected as best motion estimation and its associated deformable registration is selected as best registration.

5. The method of claim 2, wherein the deformable registration is applied after the motion estimation.

6. The method of claim 2, wherein the deformable registration and the motion estimation are applied to the high frame-rate images iteratively until a stop criterion is met.

7. The method of claim 2, wherein the motion estimation corresponds to global translational motion estimation.

8. The method of claim 2, wherein the motion estimation corresponds to affine transformation.

9. The method of claim 1, wherein said stitching the high frame-rate images is only applied to the regular images.

10. The method of claim 1, wherein information for identifying at least partial membership belonging to each stitched image is provided along with the stitching outputs.

11. The method of claim 1, further comprising removing any non-stitched image from the stitching outputs if the non-stitched image belongs to the bridging images.

12. The method of claim 1, wherein the bridging images are captured at half spatial resolution of the regular images horizontally and vertically.

13. The method of claim 1, wherein the bridging images are captured with lower bit-depth compared to the regular images.

14. A system for processing images captured from human gastrointestinal (GI) tract by a capsule camera, the system comprising one or more processors arranged to:
   receive high frame-rate images captured from human gastrointestinal (GI) tract by a capsule camera, wherein the high frame-rate images comprise regular images and bridging images, wherein the regular images and the bridging images are interleaved, and wherein the bridging images are captured with a lower spatial resolution than the regular images;
   derive motion models among the high frame-rate images based on image registration, wherein the image registration comprises target image registration between bridging images or between regular images and bridging images;
   stitch the high frame-rate images according to the motion models to generate stitching outputs comprising stitched images and non-stitched images; and
   provide the stitching outputs.

15. A method of processing images captured from human gastrointestinal (GI) tract by a capsule camera, the method comprising:
   receiving high frame-rate images captured from human gastrointestinal (GI) tract by a capsule camera, wherein the high frame-rate images comprise regular images and bridging images, wherein the regular images and the bridging images are interleaved, and wherein the bridging images are captured with a lower spatial resolution than the regular images;
   deriving motion models among the high frame-rate images based on image registration, wherein the image registration comprises target image registration between bridging images or between regular images and bridging images;
   stitching the high frame-rate images according to the motion models to generate stitching outputs comprising stitched images and non-stitched images;
   removing any non-stitched image from the stitching outputs if the non-stitched image belongs to the bridging images; and
   providing the stitching outputs.

16. A method of capturing and processing images of human gastrointestinal (GI) tract, the method comprising:
   capturing high frame-rate images using a capsule camera while the capsule camera is travelling through human gastrointestinal (GI) tract after swallowed by a human subject, wherein said capturing the high frame-rate images comprises capturing regular images and capturing bridging images, wherein the regular images and the bridging images are interleaved, and wherein the bridging images are captured with a lower spatial resolution than the regular images;
   receiving the high frame-rate images by a processing unit;
   applying image registration to the high frame-rate images by the processing unit, wherein said applying the image registration to the high frame-rate images comprises determining image registration image registration between bridging images or between regular images and bridging images;
   stitching the high frame-rate images according to motion models derived from the image registration to generate stitching outputs comprising stitched images and non-stitched images; and
   providing the stitching outputs.

17. The method of claim 16, wherein the bridging images are captured by reducing light source energy illuminating a scene in a field of view (FOV) of the capsule camera comparing to the regular images.

18. The method of claim 17, wherein the light source energy is reduced by at least half for the bridging images.

19. The method of claim 17, wherein pixel values of the regular images or the bridging images are adjusted to take into consideration of different light source energies.

20. The method of claim 16, further comprising compressing and de-compressing the high frame-rate images captured, wherein the bridging images are compressed using a higher compression ratio compared to the regular images.

21. The method of claim 16, wherein the bridging images are captured with lower bit-depth compared to the regular images.

22. The method of claim 21, wherein pixel values of the regular images or the bridging images are adjusted to take into consideration of different bit-depths.

* * * * *